(12) United States Patent
Grill et al.

(10) Patent No.: US 12,064,627 B2
(45) Date of Patent: Aug. 20, 2024

(54) SYSTEMS AND METHODS FOR TARGETED SACRAL NERVE STIMULATION

(71) Applicant: DUKE UNIVERSITY, Durham, NC (US)

(72) Inventors: Warren Grill, Durham, NC (US); James Hokanson, Durham, NC (US); Christopher Langdale, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 651 days.

(21) Appl. No.: 17/313,619

(22) Filed: May 6, 2021

(65) Prior Publication Data

US 2021/0346695 A1 Nov. 11, 2021

Related U.S. Application Data

(60) Provisional application No. 63/021,719, filed on May 8, 2020.

(51) Int. Cl.
*A61N 1/36* (2006.01)

(52) U.S. Cl.
CPC ....... *A61N 1/3606* (2013.01); *A61N 1/36007* (2013.01); *A61N 1/36135* (2013.01); *A61N 1/3615* (2013.01)

(58) Field of Classification Search
CPC .............. A61N 1/3606; A61N 1/36007; A61N 1/36135; A61N 1/3615
See application file for complete search history.

(56) References Cited

U.S. PATENT DOCUMENTS

| 2014/0378941 A1* | 12/2014 | Su | A61B 5/4255 |
| | | | 604/506 |
| 2018/0078769 A1* | 3/2018 | Dinsmoor | A61N 1/0551 |
| 2019/0001129 A1* | 1/2019 | Rosenbluth | A61N 1/08 |

OTHER PUBLICATIONS

Dieter et al., The effects of bilateral bipolar sacral neurostimulation on urinary bladder activity during filling before and after irritation in a rat model. Neurourol Urodyn. Apr. 2015;34(4):387-91.
Gonzalez et al., The effects of neuromodulation in a novel obese-prone rat model of detrusor underactivity. Am J Physiol Renal Physiol. Sep. 1, 2017;313(3):F815-F825.
Groenendijk et al., Acute effect of sacral neuromodulation for treatment of detrusor overactivity on urodynamic parameters. Neurourol Urodyn. Feb. 2020;39(2):695-701.
Hokanson et al., State-dependent bioelectronic interface to control bladder function. Sci Rep. Jan. 11, 2021;11(1):314. 15 pages.
(Continued)

*Primary Examiner* — Amanda K Hulbert
*Assistant Examiner* — Philip C Edwards
(74) *Attorney, Agent, or Firm* — Casimir Jones, S.C.; Peter J. Schlueter (57) ABSTRACT

The present disclosure provides systems and methods for targeted nerve stimulation. In particular, the present disclosure provides systems and methods for determining the location of electrode placement providing the most therapeutic benefit for a particular subject. The various embodiments disclosed herein include methods for identifying a target nerve having the strongest representation and/or the strongest subject perception associated with a peripheral nerve in a patient-specific manner.

26 Claims, 4 Drawing Sheets

(56) References Cited

OTHER PUBLICATIONS

Hokanson et al., Stimulation of the sensory pudendal nerve increases bladder capacity in the rat. Am J Physiol Renal Physiol. Apr. 1, 2018;314(4):F543-F550.

Langdale et al., Phasic activation of the external urethral sphincter increases voiding efficiency in the rat and the cat. Exp Neurol. Nov. 2016;285(Pt B):173-181.

McKenna et al., The organization of the pudendal nerve in the male and female rat. J Comp Neurol. Jun. 22, 1986;248(4):532-49.

Pastelín et al., Neural pathways of somatic and visceral reflexes of the external urethral sphincter in female rats. J Comp Neurol. Oct. 1, 2012;520(14):3120-34.

Riazimand et al., Interaction between neurotransmitter antagonists and effects of sacral neuromodulation in rats with chronically hyperactive bladder. BJU Int. Oct. 2005;96(6):900-8.

Schmidt. Applications of neurostimulation in urology. Neurourol Urodyn. 1988, 7:585-592.

Su et al., Neuromodulation in a rat model of the bladder micturition reflex. Am J Physiol Renal Physiol. Feb. 15, 2012;302(4):F477-86.

Su et al., Quantification of effectiveness of bilateral and unilateral neuromodulation in the rat bladder rhythmic contraction model. BMC Urol. Jul. 18, 2013;13:34.

Thor et al., Neural control of the female urethral and anal rhabdosphincters and pelvic floor muscles. Am J Physiol Regul Integr Comp Physiol. Aug. 2010;299(2):R416-38.

Vera et al., Conduction velocity distribution of afferent fibers innervating the rat urinary bladder. Brain Res. Jun. 18, 1990;520(1-2):83-9.

Wang et al., Neuromodulation reduces urinary frequency in rats with hydrochloric acid-induced cystitis. BJU Int. Oct. 2000;86(6):726-30.

\* cited by examiner

SYSTEMS AND METHODS FOR TARGETED SACRAL NERVE STIMULATION

RELATED APPLICATIONS

This application claims priority to and the benefit of U.S. Provisional Patent Application No. 63/021,719 filed May 8, 2020, which is incorporated herein by reference in its entirety for all purposes.

FIELD

The present disclosure provides systems and methods pertaining to targeted nerve stimulation. In particular, the present disclosure provides systems and methods for determining the location of electrode placement providing the most therapeutic benefit for a particular subject. The various embodiments disclosed herein include methods for identifying a target nerve having the strongest representation and/or the strongest subject perception with respect to a peripheral nerve in a patient-specific manner.

BACKGROUND

Sacral nerve stimulation involves electrical stimulation of a sacral nerve for treating and/or preventing various symptoms associated with diseases and conditions, including overactive bladder symptoms, urinary retention, fecal incontinence, or other disorders of bladder, bowel, or sexual function. Sacral nerve stimulation generally includes a single electrode lead—typically containing multiple individually-addressable electrode contacts along its length—implanted adjacent to one of the sacral nerves and connected to a battery-powered, implanted, pulse generator. The lower urinary tract, including the bladder, urethra, and urethral sphincters is innervated bilaterally, primarily by neurons from the sacral nerves S2, S3, and S4. The makeup of these nerves (i.e., which target organs the nerve fibers in each of the sacral nerves innervate) is known to vary between individuals and from side to side within an individual. There is currently no methodology available for choosing the sacral level and side that will be most effective (e.g., therapeutically beneficial) when targeted with electrical stimulation, as in sacral nerve stimulation. Typically electrodes are placed without regard to individual patient characteristics at S3 on one side (right or left), even though the other locations (different level or side) may be more effective. There is currently no approach, method, or rationale that can guide the choice of which side or sacral level electrical stimulation is delivered (i.e., where the stimulation lead is implanted).

SUMMARY

Embodiments of the present disclosure include a method for determining electrode location for neural stimulation in a subject. In accordance with these embodiments, the method includes electrically stimulating at least one peripheral nerve and recording electrical activity in at least one target nerve, electrically stimulating at least one target nerve and recording electrical activity in at least one peripheral nerve, and/or electrically stimulating at least one target nerve and recording at least one subject perception; and determining the at least one target nerve having the strongest representation associated with the at least one peripheral nerve and/or the strongest subject perception associated with the at least one peripheral nerve.

In some embodiments, the target nerve having the strongest representation associated with the at least one peripheral nerve and/or the strongest subject perception associated with the at least one peripheral nerve is the location determined to be where the electrode provides maximum therapeutic benefit. In some embodiments, the strongest representation associated with the at least one peripheral nerve corresponds to the largest recorded signal. In some embodiments, the strongest subject perception associated with the at least one peripheral nerve comprises one or more of location, intensity, and/or character of the perception in tissue innervated by the at least one peripheral nerve.

In some embodiments, the electrical stimulation comprises placement of an electrode lead adjacent to the target nerve or the peripheral nerve, followed by activation of a pulse generator. In some embodiments, the recording of electrical activity comprises placement of at least one electrode lead adjacent to the target nerve or placement of at least one electrode lead adjacent to the peripheral nerve, followed by detection and quantification of the electrical activity in the target nerve or the peripheral nerve.

In some embodiments, the at least one target nerve comprises a sacral nerve. In some embodiments, the at least one peripheral nerve comprises a pudendal sensory nerve. In some embodiments, the pudendal sensory nerve is a dorsal genital nerve. In some embodiments, the at least one peripheral nerve comprises a pudendal motor nerve. In some embodiments, the at least one peripheral nerve comprises a tibial nerve or a saphenous nerve.

In some embodiments, determining the at least one target nerve having the strongest representation associated with the at least one peripheral nerve comprises determining a sacral nerve side and level in the subject.

In some embodiments, the at least one subject perception corresponds to a specific location on the subject's body. In some embodiments, the specific location on the subject's body comprises an area of the subject's genitals and/or pelvic muscles.

In some embodiments, the therapeutic benefit provided by the method comprises treating and/or preventing at least one symptom associated with overactive bladder, urge urinary incontinence, urinary urgency frequency, underactive bladder, urinary retention, fecal incontinence, constipation, and/or sexual dysfunction.

In some embodiments, the method further comprises placing an electrode lead adjacent to the target nerve having the strongest representation associated with the at least one peripheral nerve.

In some embodiments, the method further comprises delivering electrical stimulation to the target nerve to treat and/or prevent at least one symptom associated with overactive bladder, urge urinary incontinence, urinary urgency frequency, underactive bladder, urinary retention, fecal incontinence, constipation and/or sexual dysfunction.

Embodiments of the present disclosure include a method of treating and/or preventing at least one symptom associated with a disease or condition. In accordance with these embodiments, the method includes determining an electrode location for neural stimulation in a subject by electrically stimulating at least one peripheral nerve and recording electrical activity in at least one target nerve, electrically stimulating at least one target nerve and recording electrical activity in at least one peripheral nerve, and/or electrically stimulating at least one target nerve and recording at least one subject perception; determining the at least one target nerve having the strongest representation associated with the at least one peripheral nerve and/or the strongest subject perception associated with the at least one peripheral nerve; and placing an electrode in an area suitable to deliver electrical stimulation to the target nerve to treat and/or prevent at least one symptom in the subject.

In some embodiments, the target nerve having the strongest representation associated with the at least one peripheral nerve and/or the strongest subject perception associated with the at least one peripheral nerve is the location determined to be where the electrode provides maximum therapeutic benefit. In some embodiments, the strongest representation associated with the at least one peripheral nerve corresponds to the largest recorded signal. In some embodiments, the strongest subject perception associated with the at least one peripheral nerve comprises one or more of location, intensity, and/or character of the perception in tissue innervated by the at least one peripheral nerve.

In some embodiments, the recording of electrical activity comprises placement of at least one electrode lead adjacent to the target nerve or placement of at least one electrode lead adjacent to the peripheral nerve, followed by detection and quantification of the electrical activity in the target nerve or the peripheral nerve.

In some embodiments, the at least one target nerve comprises a sacral nerve. In some embodiments, the at least one peripheral nerve comprises a pudendal sensory nerve.

In some embodiments, determining the at least one target nerve having the strongest representation associated with the at least one peripheral nerve comprises determining a sacral nerve side and level in the subject.

In some embodiments, the at least one subject perception corresponds to a specific location on the subject's body. In some embodiments, the specific location on the subject's body comprises an area of the subject's genitals and/or pelvic muscles.

In some embodiments, the disease or condition comprises overactive bladder, urge urinary incontinence, urinary urgency frequency, underactive bladder, urinary retention, fecal incontinence, constipation and/or sexual dysfunction.

DETAILED DESCRIPTION

Embodiments of the present disclosure include systems and methods for targeted nerve stimulation. In accordance with these embodiments, the present disclosure provides systems and methods for determining the location of electrode placement providing the most therapeutic benefit for a particular subject. The various embodiments disclosed herein include methods for identifying a target nerve having the strongest representation and/or the strongest subject perception with respect to a peripheral nerve in a patient-specific manner.

As described further herein, the present disclosure provides systems and methods for determining the location for placement of an electrode based on the side (right or left) and sacral level that contains the strongest representation of a particular component of a peripheral nerve or peripheral nerve branch, and/or the strongest subject perception associated with a particular component of a peripheral nerve or peripheral nerve branch. The various embodiments described herein include non-limiting examples of identifying and determining a location for electrode placement based on the side and sacral level that contains the strongest representation and/or most robust subject perception associated with the pudendal sensory nerve. However, it is to be understood that the methods and systems described herein can also be applied to other peripheral nerves or nerve branches, for example identifying the nerve root that contains the strongest representation of the pudendal motor nerve or the strongest representation of the branch of the pudendal nerve innervating the external urethral sphincter, among others. Further, the exemplary methods of using sacral nerve stimulation, and the associated electrode placement methods, is described in the context of treatment of overactive bladder/urinary incontinence. However, the systems and methods described herein can also apply to other conditions, such as disorders of bladder, bowel, sexual function, etc.

In one aspect, the present disclosure provides a novel method for selecting the location for implantation of an electrode for nerve stimulation. In some embodiments, the method comprises determining the location on the subject (e.g., a target nerve) that contains the most robust representation with respect to a peripheral nerve, and administering the stimulation at that location. The location on the subject includes the side of a subject's sacrum (e.g., right or left) and/or the sacral level of the subject. For example, stimulation of the pudendal sensory nerve for treating overactive bladder is described. The pudendal sensory nerve is constituted of axons originating from parts of the S2, S3, and S4 sacral nerves. Like the target organs, the relative contribution of each sacral nerve to the pudendal sensory nerve (and other peripheral nerves) varies between individuals and from side to side within an individual. Electrical stimulation of the pudendal sensory nerve is known to provide therapeutic relief similar to, and perhaps superior to, sacral nerve stimulation. However, pudendal sensory stimulation, which requires a different and more complicated surgical approach, is generally not used in clinical practice. Stimulation of the pudendal sensory nerve drives the therapeutic benefits of sacral nerve stimulation. Therefore, stimulation of the sacral nerve (side and level) that has the strongest representation of pudendal sensory neurons will provide a superior therapeutic benefit compared to stimulation of other candidate locations (side and level).

As described further herein, the present disclosure provides multiple methods to determine which location (side and level) has the strongest representation of a peripheral nerve or branch (e.g., the pudendal sensory nerve). Sacral nerve stimulation, typically, is achieved with electrodes placed through holes in the sacrum (sacral foramen) that allows the electrodes to be near (e.g., adjacent to) the nerve of interest. It may also be possible to perform the analytical testing by placing electrodes on the surface of the skin (lower back area) over the foramen.

These methods include, but are not limited to, the following three embodiments, which can be performed separately from each other to assess the therapeutic needs of a subject, or in combination with each other, as part of an integrated treatment regimen or protocol. In one embodiment, the method includes recording the electrical activity over or within each sacral foramen (location) from electrical stimulation of pudendal sensory nerve fibers (e.g., dorsal genital nerve fibers) from a peripheral location. The location with the largest recorded signal is generally considered to be the strongest representation of the pudendal sensory nerve, and thus it is targeted for electrode placement/implantation and therapeutic sacral nerve stimulation. In another embodiment, the method includes recording activation of pudendal sensory nerve fibers (e.g., dorsal genital nerve fibers) from electrical stimulation delivered over or within each sacral foramen. The location that evokes the largest recorded signal at the pudendal sensory nerve has the strongest representation of the pudendal sensory nerve, and thus it is targeted for electrode placement/implantation and therapeutic sacral nerve stimulation. In another embodiment, the method includes subject self-reporting of the location, intensity, and character of perceptions evoked by electrical stimulation delivered over or within each sacral foramen. The location that evokes the strongest subject perception specific to locations on the body innervated by the pudendal sensory nerve (e.g., genitalia, clitoris in a female, glans of the penis in a male) has the most representation of the pudendal sensory nerve, and thus it is targeted for electrode implantation and therapeutic sacral nerve stimulation.

Section headings as used in this section and the entire disclosure herein are merely for organizational purposes and are not intended to be limiting.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"About" is used to provide flexibility to a numerical range endpoint by providing that a given value may be "slightly above" or "slightly below" the endpoint without affecting the desired result.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated. Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (e.g., a monkey, such as a cynomolgus or rhesus monkey, chimpanzee, etc.) and a human). In some embodiments, the subject may be a human or a non-human. In one embodiment, the subject is a human. The subject or patient may be undergoing various forms of treatment.

"Treat," "treating" or "treatment" are each used interchangeably herein to describe reversing, alleviating, or inhibiting the progress of a disease and/or injury, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the seventy of a disease prior to affliction refers to administration of a treatment to a subject that is not at the time of administration afflicted with the disease. "Preventing" also refers to preventing the recurrence of a disease or of one or more symptoms associated with such disease.

The term "effective amount" or "therapeutically effective amount" refers to an amount sufficient to effect beneficial or desirable biological and/or clinical results.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, neurobiology, microbiology, genetics, electrical stimulation, neural stimulation, neural modulation, and neural prosthesis described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. METHODS AND SYSTEMS

Embodiments of the present disclosure include methods for determining the location for placement and/or implantation of an electrode based on the side (right or left) and sacral level that contains the strongest representation of a particular component of a peripheral nerve or peripheral nerve branch. As provided in the Examples, experiments were conducted to investigate the stimulation and recording parameters of the S1 sacral nerve in rats; however, the methods described herein can be applied to other sacral nerves, such as S2, S3, and S4 sacral nerves. Additionally, the inventive concepts of the present disclosure can be applied to other peripheral nerves or nerve branches, for example, identifying the nerve root that contains the strongest representations of the pudendal motor nerve or the strongest representation of the branch of the pudendal nerve innervating the external urethral sphincter. Although the use of sacral nerve stimulation to determine electrode placement is exemplified herein for treatment of overactive bladder/ urinary incontinence, the inventive concepts of the present disclosure also apply to other disorders of bladder, bowel, or sexual function. The results provided herein demonstrate the feasibility of using the methods of the present disclosure to determine empirically electrode location for maximum therapeutic benefit in a human subject.

In accordance with these embodiments, the present disclosure provides methods for determining electrode location for neural stimulation in a subject. In some embodiments, the method includes electrically stimulating at least one peripheral nerve and recording electrical activity in at least one target nerve, and then determining which target nerve has the strongest representation associated with the peripheral nerve. In some embodiments, the method includes electrically stimulating at least one target nerve and recording electrical activity in at least one peripheral nerve, and then determining which target nerve has the strongest representation associated with the peripheral nerve. In some embodiments, the method includes electrically stimulating at least one target nerve and recording at least one subject perception, and determining which target nerve has the strongest subject perception associated with the peripheral nerve. Each of these methods include can be performed separately from each other to assess the therapeutic needs of a subject, or in combination with each other, as part of an integrated treatment regimen or protocol.

Using this approach, the target nerve with the strongest representation associated with the at least one peripheral nerve and/or the strongest subject perception associated with the at least one peripheral nerve can be determined. Generally, this target nerve will be the location where an electrode is to be placed and/or implanted to provide maximum therapeutic benefit to a subject. In some embodiments, the strongest representation associated with the at least one peripheral nerve corresponds to the largest recorded signal. In some embodiments, the strongest subject perception associated with the at least one peripheral nerve comprises one or more of location, intensity, and/or character of the perception in tissue innervated by the at least one peripheral nerve.

As described further herein, carrying out the methods of the present disclosure involve electrical stimulation of either a target nerve or a peripheral nerve. Generally, electrical stimulation includes placement of an electrode lead adjacent to the target nerve or the peripheral nerve, followed by activation of a pulse generator. Additionally, carrying out the methods of the present disclosure involve recording electrical activity in a target or peripheral nerve. Generally, recording electrical activity includes placement of at least one electrode lead adjacent to the target nerve or the peripheral nerve, followed by detection and quantification of the electrical activity in the target nerve or the peripheral nerve.

In some embodiments, target nerve recording involves placing an electrode in close proximity to the tissue and recording the activation as a function of increasing stimulation amplitudes at the various target sites. At some point, increasing the amplitude leads to neural activation, as measured on the recording electrode. Typically, this is a voltage deflection and is measured by averaging the response just after a pulse for multiple pulses. Then, the activity is generally quantified by taking the average rectified value for some period of time after the stimulus. In some cases, this time window is generic or wide, and in other cases, specific time windows or bins can be analyzed, as different types of nerve fibers (with specific functions) have different diameters and those diameters conduct ("travel") at different speeds. Thus, by measuring different response times, assessments can be made pertaining to how different populations of nerve fibers reach a recording electrode. It may be possible that one nerve tends to send more rapidly conducting fibers and another nerve more slowly conducting fibers, and what is desired is the largest activation of slower fibers (which would be analyzed by examining the response over a specific time window). These responses are generally referred to as "compound action potentials" because the recording represents the activity of multiple nerve fibers together, where each fiber transmits a signal called an action potential.

At some amplitude, no response is visible, which generally indicates that a target nerve does not send nerve fibers to a peripheral nerve. In other cases, a certain amplitude causes activation, at which point the amplitude is increased until the response becomes saturated (e.g., an increase in stimulation amplitude that does not result in an increase in the amplitude of the response). If activation and saturation are obtained on multiple channels, it is possible to compare which stimulation channel elicits the largest activation (largest recording). Generally, obtaining saturation (in contrast to comparing absolute stimulus amplitudes) allows amplitude to be determined based on how close the stimulation electrode is to the nerve, whereas the magnitude of the response at the saturation level is a function of how many nerve fibers reach the recording site (which is the desired measurement of the methods provided herein). Generally, it is more difficult to have multiple recording sites (and 1 stimulation site), as it can be more difficult to compare recordings in this manner. In this case, the more feasible approach is to identify one site that has a response at an amplitude at which other sites do not show a response, i.e., the threshold for said one site is lower than the threshold for the one or more other sites.

As would be recognized by one of ordinary skill in the art based on the present disclosure, these methods described herein can be applied to various nerve networks, as long as it is feasible to stimulate and record as described above. In some embodiments, the methods of the present disclosure are useful for determining the most therapeutically beneficial site for sacral nerve stimulation (e.g., the target nerve being a sacral nerve). Generally, the lumbosacral plexus is a network of nerve fibers that innervates the skin, muscles, viscera, organs, and visceral organs of the pelvis and lower limb. It is located on the surface of the posterior pelvic wall, anterior to the piriformis muscle. The plexus is formed by the anterior rami (divisions) of the sacral spinal nerves S1, S2, S3 and S4. It also receives contributions from the lumbar spinal nerves L4 and L5. The spinal nerves S1-S4 form the basis of the sacral plexus. At each vertebral level, paired spinal nerves exit the spinal cord via the intervertebral foramina of the vertebral column. Each nerve then divides into anterior or ventral and posterior or dorsal nerve fibers. The lumbosacral plexus begins as the anterior fibers of the spinal nerves S1, S2, S3, and S4. They are joined by the 4th and 5th lumbar roots, which combine to form the lumbosacral trunk. This descends into the pelvis to meet the sacral roots as they emerge from the spinal cord.

The anterior rami of the S1-S4 spinal roots (and the lumbosacral trunk) divide into several cords. These cords then combine together to form the five major peripheral nerves of the lumbosacral plexus. These nerves then descend down the posterior pelvic wall and innervate the pelvis via the greater sciatic foramen (these nerves enter the gluteal region of the lower limb, innervating the structures there), or they remain in the pelvis (these nerves innervate the pelvic muscles, organs and perineum).

There are several branches of the lumbosacral plexus. The superior gluteal nerve leaves the pelvis via the greater sciatic foramen, entering the gluteal region superiorly to the piriformis muscle. It is accompanied by the superior gluteal artery and vein for much of its course. It innervates the gluteus minimus, gluteus medius and tensor fascia. The inferior gluteal nerve leaves the pelvis via the greater sciatic foramen, entering the gluteal region inferiorly to the piriformis muscle. It is accompanied by the inferior gluteal artery and vein for much of its course, and it innervates the gluteus maximus. The tibial portion of the sciatic nerve innervates the muscles in the posterior compartment of the thigh (apart from the short head of the biceps femoris), and the hamstring component of adductor magnus. It innervates all the muscles in the posterior compartment of the leg and sole of the foot. The tibial portion supplies the skin of the posterolateral leg, lateral foot and the sole of the foot. The common fibular portion of the sciatic nerve innervates the short head of biceps femoris, all muscles in the anterior and lateral compartments of the leg and extensor digitorum brevis. It supplies the skin of the lateral leg and the dorsum of the foot.

The posterior cutaneous nerve of thigh leaves the pelvis via the greater sciatic foramen, entering the gluteal region inferiorly to the piriformis muscle. It descends deep to the gluteus maximus and runs down the back of the thigh to the knee. It innervates the skin on the posterior surface of the thigh and leg, and also innervates the skin of the perineum.

The pudendal nerve leaves the pelvis via the greater sciatic foramen, then re-enters via the lesser sciatic foramen. It moves anterosuperiorly along the lateral wall of the ischiorectal fossa, and terminates by dividing into several branches. It innervates the skeletal muscles in the perineum, the external urethral sphincter, the external anal sphincter, levator ani (motor functions). It also innervates the penis and the clitoris and most of the skin of the perineum (sensory functions). The pudendal nerve originates from the S2, S3, and S4 sacral nerve roots. The main trunk of the pudendal nerve takes an extrapelvic course superficial to the coccygeus muscle. The main trunk passes over the ischial spine and enters Alcock's (pudendal) canal. In the upper half of the pudendal canal, the pudendal nerve gives rise to the inferior rectal nerve. The inferior rectal nerve exits the pudendal canal medially and extends motor and sensory branches. Motor branches innervate the levator ani, and the cutaneous branches innervate the perianal skin and the scrotum or labia. The inferior rectal nerve terminates in multiple branches to the external anal sphincter. At the end of the pudendal canal, the pudendal nerve gives rise to two branches, the perineal nerve and the deep dorsal nerve of the clitoris or penis. The deep dorsal nerve continues as a terminal branch to the penis or clitoris. The perineal nerve divides into the scrotal or labial branch and two muscular branches to the bulbocavernosus and the striated urethral sphincter.

In addition to the five major nerves of the lumbosacral plexus, there are a number of smaller branches. These tend to be nerves that directly supply muscles (with the exception of the perforating cutaneous nerve, which supplies the skin over the inferior gluteal region and the pelvic splanchnic nerves, which innervate the abdominal viscera), and include the nerve to the piriformis, the nerve to the obturator internus, and the nerve to quadratus femoris.

In some embodiments, at least one target nerve comprises a sacral nerve. In some embodiments, at least one peripheral nerve comprises a pudendal sensory nerve. In some embodiments, the pudendal sensory nerve is a dorsal genital nerve. The dorsal nerve of the penis or clitoris is a smaller terminal branch of the pudendal nerve. It runs forward first in the pudendal canal above the internal pudendal vessels and then in the deep perineal space between these vessels and the pubic arch.

In some embodiments, the at least one peripheral nerve comprises a pudendal motor nerve. In some embodiments, the at least one peripheral nerve comprises a tibial nerve or a saphenous nerve. The tibial nerve is a branch of the sciatic nerve, and it arises at the apex of the popliteal fossa. It travels through the popliteal fossa, giving off branches to muscles in the superficial posterior compartment of the leg. The saphenous nerve is the largest and terminal branch of the femoral nerve. Shortly after the femoral nerve passes under the inguinal ligament, it splits into anterior and posterior divisions by the passage of the lateral femoral circumflex artery (a branch of the profunda femoris artery).

In some embodiments, determining the at least one target nerve having the strongest representation associated with the at least one peripheral nerve comprises determining a sacral nerve side (right of left side of the subject) and level in the subject (S2, S3, or S4 nerves). As described further herein, determining the sacral nerve side and level informs placement of a stimulatory electrode for treating a disease or condition. In some embodiments, the therapeutic benefit provided by the method comprises treating and/or preventing at least one symptom associated with overactive bladder, urge urinary incontinence, urinary urgency frequency, underactive bladder, urinary retention, fecal incontinence, constipation, and/or sexual dysfunction.

In some embodiments, the method includes electrically stimulating at least one target nerve and recording at least one associated perception from the subject upon stimulation. In some embodiments, the subject's perception corresponds to a part of the subject's body innervated by a peripheral nerve that is associated with the target nerve, such that the strongest or most robust subject perception indicates that the target nerve is strongly associated with that peripheral nerve. In some embodiments, the strongest subject perception associated with at least one peripheral nerve comprises one or more of location, intensity, and/or character of the perception in tissue innervated by the at least one peripheral nerve. In some embodiments, the specific location on the subject's body comprises an area of the subject's genitals and/or pelvic muscles. In some embodiments, the method further comprises placing an electrode lead adjacent to the target nerve having the strongest representation associated with the at least one peripheral nerve and delivering electrical stimulation to the target nerve to treat and/or prevent at least one symptom associated with overactive bladder, urge urinary incontinence, urinary urgency frequency, underactive bladder, urinary retention, fecal incontinence, constipation and/or sexual dysfunction.

3. THERAPEUTIC METHODS

Embodiments of the present disclosure include a method of treating and/or preventing at least one symptom associated with a disease or condition. In accordance with these embodiments, the method includes determining an electrode location for neural stimulation in a subject by electrically stimulating at least one peripheral nerve and recording electrical activity in at least one target nerve, by electrically stimulating at least one target nerve and recording electrical activity in at least one peripheral nerve, and/or by electrically stimulating at least one target nerve and recording at least one subject perception. The method also includes determining which target nerve has the strongest representation associated with the at least one peripheral nerve and; or the strongest subject perception associated with the at least one peripheral nerve, and placing an electrode in an area suitable to deliver electrical stimulation to the target nerve to treat and/or prevent at least one symptom in the subject. Each of these approaches for determining the target nerve having the strongest representation associated with at least one peripheral nerve and/or the strongest subject perception associated with at least one peripheral nerve can be performed separately from each other to assess the therapeutic needs of a subject, or in combination with each other, as part of an integrated treatment regimen or protocol. The therapeutic information obtained from these methods can then be used to address the specific therapeutic needs of a subject and thereby provide enhanced therapeutic benefit.

In some embodiments, the target nerve having the strongest representation associated with the at least one peripheral nerve and/or the strongest subject perception associated with the at least one peripheral nerve is the location where the electrode provides maximum therapeutic benefit. In some embodiments, the strongest representation associated with the at least one peripheral nerve corresponds to the largest recorded signal. In some embodiments, the strongest subject perception associated with the at least one peripheral nerve comprises one or more of location, intensity, and/or character of the perception in tissue innervated by the at least one peripheral nerve.

In some embodiments, the recording of electrical activity comprises placement of at least one electrode lead adjacent to the target nerve or placement of at least one electrode lead adjacent to the peripheral nerve, followed by detection and quantification of the electrical activity in the target nerve or the peripheral nerve. In some embodiments, the at least one target nerve comprises a sacral nerve. In some embodiments, the at least one peripheral nerve comprises a pudendal sensory nerve. In some embodiments, determining the at least one target nerve having the strongest representation associated with the at least one peripheral nerve comprises determining a sacral nerve side and level in the subject. In some embodiments, the at least one subject perception corresponds to a specific location on the subject's body. In some embodiments, the specific location on the subject's body comprises an area of the subject's genitals and/or pelvic muscles.

In some embodiments, the disease or condition comprises overactive bladder, urge urinary incontinence, urinary urgency frequency, underactive bladder, urinary retention, fecal incontinence, constipation and/or sexual dysfunction. In some embodiments, placing an electrode lead adjacent to the target nerve determined to have the strongest representation and/or strongest subject perception associated with a peripheral nerve, and delivering electrical stimulation to the target nerve treats and/or prevents at least one symptom associated with overactive bladder, urge urinary incontinence, urinary urgency frequency, underactive bladder, urinary retention, fecal incontinence, constipation and/or sexual dysfunction.

In some embodiments, systems for treating and/or preventing at least one symptom of a disease or conditions includes an electrode sized and configured for placement or implantation in proximity to a target nerve (e.g., a sacral nerve), and a pulse generator coupled to the electrode. In some embodiments, the pulse generator includes a power source comprising a battery and a microprocessor coupled to the battery. In accordance with these embodiments, the systems allow for programming the pulse generator to output a given stimulation pattern (e.g., on a graphical user interface (GUI)) to treat a subject.

In some embodiments, an electrode or lead can be placed in a desired position in contact with a target nerve of a subject. In one embodiment, the electrode can be implanted in a region adjacent to a sacral nerve (e.g., sacral foramen). However, as would be recognized by one of ordinary skill in the art based on the present disclosure, the electrode can be placed or implanted in, on, or near a target nerve for the purpose of stimulation to achieve a therapeutic purpose. In addition, the electrode may be utilized for transcutaneous stimulation where electrodes are placed, not subcutaneous, but on an outer skin surface.

The pulse generator can include stimulation generation circuitry, which can include an on-board, programmable microprocessor, which has access to and/or carries embedded code. The code expresses pre-programmed rules or algorithms under which desired electrical stimulation is generated, having desirable electrical stimulation parameters that may also be calculated by the microprocessor, and distributed to the electrode(s) on the lead. According to these programmed rules, the pulse generator directs the stimulation through the lead to the electrode(s), which serve to selectively stimulate the target nerve. The code may be programmed, altered or selected by a clinician to achieve the particular physiologic response desired. Additionally or alternatively to the microprocessor, stimulation generation circuitry may include discrete electrical components operative to generate electrical stimulation having desirable stimulation parameters. One or more of the parameters may be prescribed or predetermined as associated with a particular treatment regime or indication. In some embodiments, the pulse generator can be programed to output a stimulation pattern (e.g., on a graphical user interface (GUI)).

In some embodiments, the system also includes an external computing device that is not implanted within the subject. The computing device can communicate with a simulation device or system via any suitable communication link (e.g., a wired, wireless, or optical communication link). The communication link may also facility battery recharge. A clinician may interact with a user interface of the computing device for programming the output of the implanted pulse generator, including the electrodes that are active, the stimulation pulse amplitude, the stimulation pulse duration, the stimulation pattern (including pulse repetition frequency), and the like, applied via each electrode contact to each sub-population.

4. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

Experiments were established to investigate the stimulation and recording parameters of the present disclosure using the rat model system. The methods used are similar to those reported previously (Hokanson et al., 2021). Experiments were conducted in 39 rats, 1 male Charles-Dawley (CD) rat (sacral foramen testing), 2 female Wistar rats (sacral foramen testing), 17 female CD rats (age: 16.1 weeks [13.4-24.1], median, range; weight: 269 g [239-314]), 11 female obese prone (OP) rats (age: 30 weeks [29-32.3]; weight: 487 g [428-545]), and 8 obese-resistant (OR) rats (age: 26.15 weeks [25.7-26.9]; weight: 254 g [244-284]). The CD and Wistar rats were ordered from Charles River. OP and OD breeders were originally obtained from Charles River, and the rats used in these studies were bred from a colony at Duke University. The OP and OR rats were on a standard diet for 8.1-13.9 weeks (median 12.6 weeks) after birth. Thereafter, animals were switched to a high-fat diet (60 kcal % fat, D12492, Research Diets) and remained on the high fat diet for at least 15 weeks, at which time experiments began on this cohort. Median time on the high-fat diet was 17.3 weeks (range: 15.1-18.4 weeks).

Animals were anesthetized with urethane (1.2 g/kg SC, supplemented as necessary). In later OP experiments with pudendal motor bursting the initial dose was reduced to 1.1 g/kg SC due to concern that the high urethane dosage (due to the heavy body weight) was influencing reflex bladder contractions. Body temperature was monitored using an esophageal temperature probe and maintained at 36-38° C. with a water blanket. Heart rate and arterial blood oxygen saturation levels were monitored using a pulse oximeter (Nonin Medical, 2500A VET).

The bladder was exposed via a midline abdominal incision. The tip of a polyethylene (PE-90) catheter (Clay Adams, Parsippany, N.J) was heated to create a collar and inserted into the bladder lumen through a small incision in the apex of the bladder dome and secured with 6-0 silk suture. After EMG electrode placement (next paragraph) the abdominal wall was closed in layers with 3-0 silk suture. The bladder catheter was connected via a 3-way stopcock to an infusion pump (Harvard Apparatus PHD 4400) and to a pressure transducer (ArgoTrans, Argon Medical Devices Inc., Plano, TX) connected to a bridge amplifier and filter (100 Hz low-pass, Model 13-6615-50, Gould Instruments, Valley View, OH) for measuring intravesical pressure. Pressure data were sampled at 1 kHz using a PowerLab system (AD Instruments, Colorado Springs, CO).

Figures 1A, 1B, 1C, 1D, 1E, 1F, 1G, 1H, 1I, 1J:
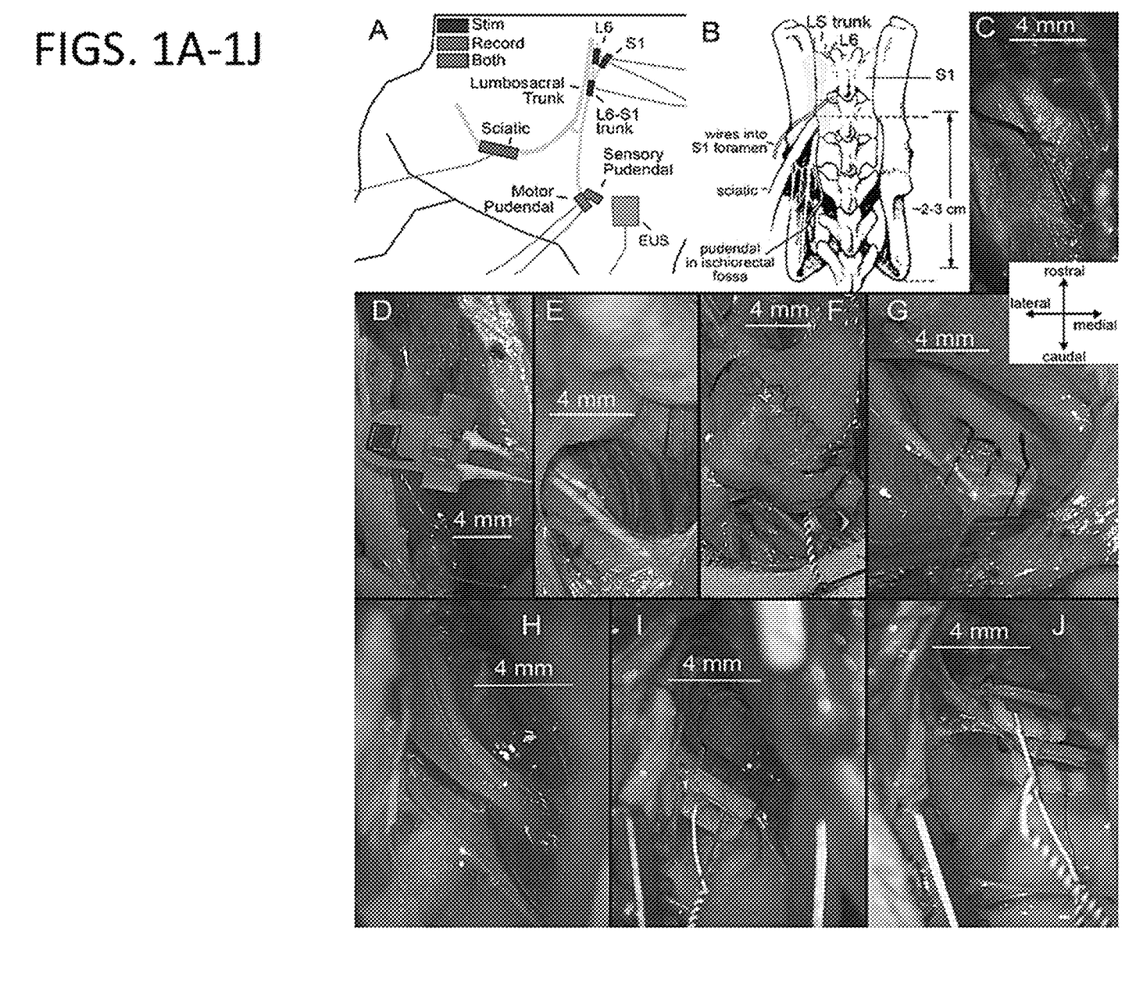
FIGS. 1A-1J: Representative diagram of nerve interfaces of the L6-S1 sacral region, which includes sacral nerves S1, S2, S3, and S4 (A). All interfaces were placed with the animal in the prone position (dorsal approach), with the exception of the EUS electrode. Diagram showing the pelvis and a portion of the spinal column (B). Interfacing with the pudendal nerve was done in the ischiorectal fossa. The yellow portion highlights where bone was removed to access the spinal nerves. Adapted from (McKenna and Nadelhaft, 1986). Photo showing placement of wires into the S1 foramen (C). Photo of the electrode used to record EUS EMG (D). Fat and connective tissue covering the proximal urethra has been cleared for placement of the EUS electrode (E). The electrode has been placed on top of the urethra and below the pubic symphysis (F). The sciatic nerve cuff has been placed but has not yet been closed with additional suture (G). Just distal to the cuff is the split of the sciatic into the peroneal and tibial nerves. Photo of the ischiorectal fossa prior to cuff placement (H). The sensory pudendal nerve is clearly visible at the rostral portion of the connective tissue. The motor pudendal nerve is barely visible at the caudal portion. A nerve cuff has been placed around both the sensory and motor nerves (I). In later experiments cuffs were placed separately around the sensors (upper left) and motor (lower right) branches (J). For mechanical stability the internal pudendal vein (always) and artery (generally) were placed in the same cuff as the motor pudendal nerve.

External urethral sphincter (EUS) EMG was measured using a bipolar paddle electrode (Micro-Leads Neuro, Boston) placed intra-abdominally between the urethra and the pubic symphysis (Hokanson et al., 2018) (FIGS. 1D-1F). EUS EMG leads were connected through a preamplifier (HIP5, Grass Products, Warwick, RI) to an amplifier (P511, Grass Products). A subcutaneous needle served as ground. Signals were filtered (3 Hz-3 kHz) and sampled at 20 kHz.

After preparation of the animals, experiments were conducted using electrodes for nerve stimulation and recording. After placing the bladder catheter and EUS EMG electrodes, the animal was turned to a prone position for placement of peripheral neural interfaces. The order of nerve cuff placement involved first placing a sciatic nerve cuff, exposure of the pudendal nerves for cuff placement, exposure of the spinal nerves for cuff placement, placement of the pudendal nerve cuff(s), and placement of the spinal nerve cuff(s).

In experiments that included instrumentation of the sciatic nerve, a skin incision was made along the length of the thigh and muscles were blunt dissected to expose the sciatic nerve. After separating the nerve from surrounding connective tissue using forceps a 1 mm inner diameter 5 mm length nerve cuff (MicroProbes, Gaithersburg, MD) was placed around the nerve (FIG. 1G). A knot was tied around the cuff with 6-0 suture to close the cuff. The muscles were then allowed to fall back into place over the cuff, and 3-0 silk suture was used to loosely close the skin.

For pudendal nerve cuff placement, a skin incision was made down the midline of the lower back and the gluteal muscles were resected from the midline. The ischium was spread apart from the sacrum to expose the ischiorectal fossa (FIG. 1H). Then either the compound pudendal nerve, consisting of the sensory and motor branches, or in other experiments the sensory and motor nerve branches individually, were dissected from surrounding tissue with fine forceps. When isolating either the motor nerve, or the compound pudendal nerve, the nerves were not dissected free from surrounding blood vessels. Bipolar cuff electrodes (Micro-Leads) were placed either on the compound pudendal nerve (0.8 mm inner diameter 3 mm length, FIG. 1I), the sensory pudendal nerve (initially 0.4 mm inner diameter 3 mm length and later 0.3 mm inner diameter 2 mm length), or both the sensory and motor pudendal nerves (0.4 mm inner diameter 3 mm length for the motor pudendal cuff, FIG. 1J), depending on the experiment type. After nerve cuff placement the spreaders were removed, allowing the cavity to close.

For spinal nerve stimulation, a midline skin incision was made and the back muscles over the sacrum were resected. Several nerves from dorsal rami run along the dorsal surface of the sacrum innervating the surrounding tissue and running into each other. These nerves were cut (generally via cauterization) to avoid pulling on the underlying ventral rami that innervate the lower urinary tract.

For stimulation of the S1 nerve, via the S1 foramen, two wires were advanced in a medio-rostral direction for 1-2 mm past their initial entrance into the foramen. These wires consisted of four twisted strands of stainless steel wire (AS644, Cooner Wire, Chatsworth, CA). The ends of the wire were cut with no additional removal of the insulation. The ends were placed such that one wire was recessed 1 mm from the other. The wires were held together at multiple locations along their length using knots tied with 6-0 silk suture. Cutting the dorsal nerves caused the remaining ventral portion to recede into the sacral foramen, allowing for easier wire insertion. Had the nerves not been cut there was no clear approach for placing the wires into the foramen without puncturing the S1 dorsal ramus.

Example 2

To expose the ventral rami of the L6 and S1 nerves, as well as the L6-S1 trunk, the sacrum was cut in a rostral to caudal direction using Rongeurs. Additional bone from the sacrum was removed medial to the first cut and just caudal to the S1 foramen to expose the S1 spinal nerve and the L6-S1 trunk. Spreaders were used to separate the rostral portion of the hip bone an additional 1-2 mm from the midline to make it easier to access all relevant neural tissue. These spreaders were kept in place during testing.

Figures 2A, 2B, 2C:
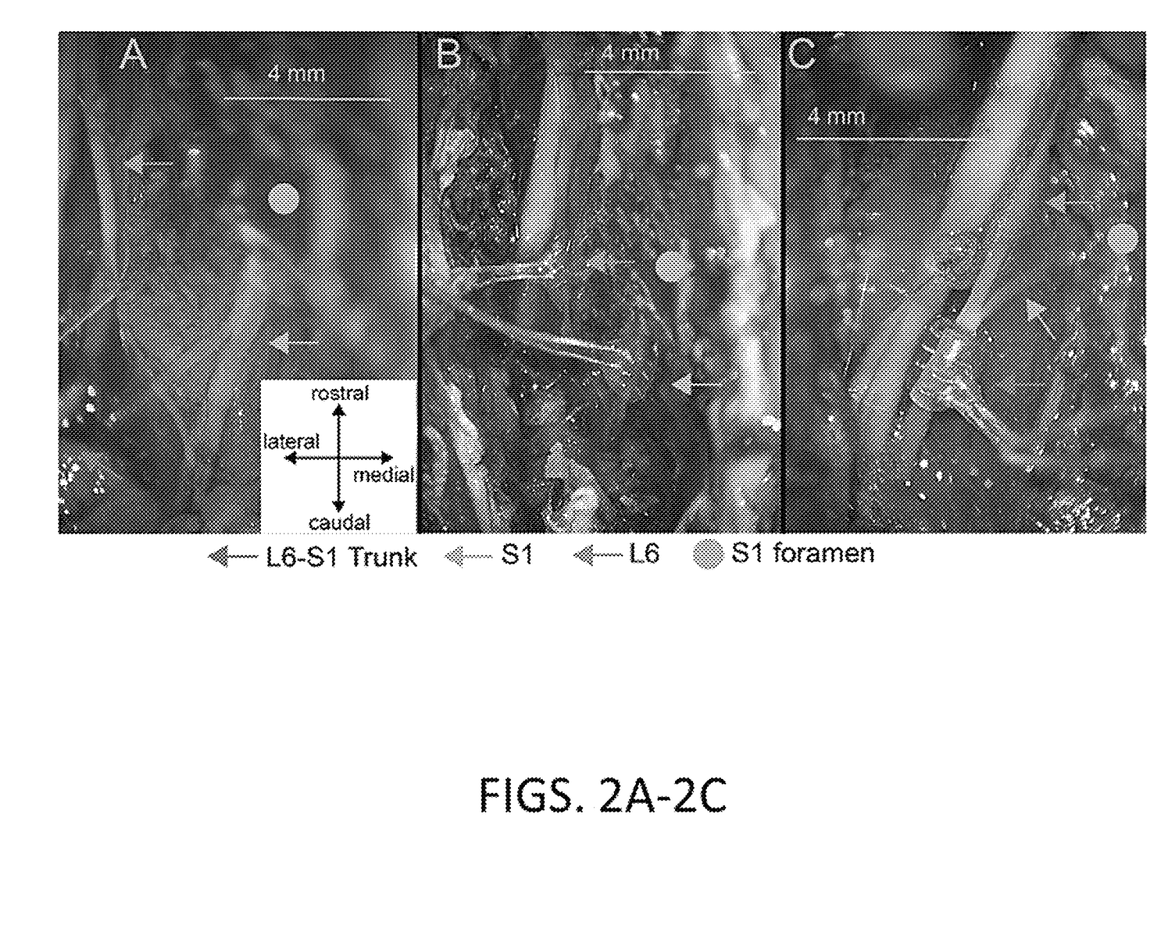
FIGS. 2A-2C: Set up for stimulation of L6, S1, and L6-S1 trunk. Photo after bone from the sacrum has been removed and muscle covering the L6 and S1 nerves has also been removed (A). This photo was taken just after the photo in B (i.e. at the end of the experiment after the nerve cuffs had been removed). The blue arrow points in the general direction of the L6-S1 trunk but the trunk is still covered by muscle tissue. Photo from the same experiment with the stimulation electrodes in place (B). Note, stimulation electrodes for S1 were placed on the entirety of the S1 nerve, not just the portion going towards the L6-S1 trunk. In cases like this experiment in which the L6 nerve merged with the lumbosacral trunk the stimulation cuff was placed distal to the merger/crossing. Photo from another experiment in which L6-S1 trunk stimulation was conducted (C). A small piece of plastic film has been placed between the lumbosacral trunk (left) and L6-S1 trunk (right) to minimize current spread.

After removing bone, a thin layer of muscle covering the nerves was removed. Fine forceps were used to dissect the neural tissue from surrounding connective tissue. Cuffs were subsequently placed around the S1 and L6 spinal nerves (FIG. 2B). In two initial experiments, a loose 0.3 mm inner diameter 2 mm length CorTec cuff was used on the S1 nerve and a 0.8 mm inner diameter 3 mm length MicroLeads cuff was used on the L6 nerve. In the subsequent two experiments, 0.75 mm inner diameter 1.6 mm length Microprobes cuffs was used on both nerves (tripolar, 0.4 mm spacing between sites, outside leads shorted together). Finally, a switch was made to 0.5 mm inner diameter 1.6 mm length MicroProbes cuffs (same design as the 0.75 mm inner diameter 1.6 mm length cuffs) for the remaining experiments. A 0.75 mm inner diameter 1.6 mm length MicroProbes cuff was used on the L6-S1 trunk (FIG. 2C). Unlike the sciatic nerve cuff, these MicroProbes cuffs were not closed with suture as during initial testing, as this proved to be difficult to perform properly. During L6-S1 trunk stimulation plastic wrap was placed between the L6-S1 trunk and the lumbosacral trunk to minimize off-target activation.

In experiments in which portions of the sacrum were resected, saline was placed over the nerves to prevent drying. Additionally, plastic wrap was placed over the wound to keep heat and moisture in.

In experiments in which the animal was paralyzed, the trachea was exposed prior to opening the abdomen or placing nerve cuffs. The trachea was blunt-dissected from surrounding tissue and a 4-0 silk suture was placed around the trachea (but left untied). Subsequently, a slit was made in the upper half of the trachea, between cartilage rings, using small surgical scissors, just caudal to the thyroid gland. A blunted, angled needle was placed roughly 1 cm into the trachea and secured with the suture. Surrounding muscle and skin were sutured closed (3-0 silk) and a small tie was wide around the base of the needle, affixing the needle to the skin of the chin.

Just prior to paralysis the animal was placed on a ventilator (PhysioSuite, Kent Scientific). Tidal volume, respiratory rate, and pressure were adjusted by the device based on body weight. 1 ml of saline containing gallamine triethiodide (20 mg, Sigma) was injected IP. In the first experiment stimulation testing began roughly 5 minutes after injection. Subsequent analysis suggested that paralysis was incomplete. In subsequent experiments if paralysis appeared to be complete, the stimulation amplitude was doubled to confirm. This process was repeated until doubling failed to evoke discernible EMG activity on the EUS electrode. Every hour an additional bolus of 20 mg gallamine triethiodide was administered. Immediately after testing the animal was euthanized by injection with a bolus of urethane (0.6 g/kg, IP) and a bilateral thoracotomy.

Experiments were then conducted to investigate stimulation from the S1 foramen. In four animals (1 male, 3 female) stimulation of the S1 nerve was conducted with wires placed through the S1 foramen. Stimulation amplitude was varied while recording from the EUS (n=4), sciatic nerve (n=3), and compound pudendal nerve (n=2). This was done without paralysis. In a fifth experiment only EUS EMG and the S1 stimulation wires were placed and cystometric testing, with and without stimulation (1 T or 1× the amplitude at which stimulation evoked a motor response). Stimulation for these experiments generally consisted of 23 Hz stimulation with biphasic pulses, 40 vs per phase. 23 Hz was chosen based on it being a relatively high rate—to minimize the time necessary to collect a large number of pulses for averaging—and for not being a divisor of 60—to help reduce 60 Hz noise during stimulus-triggered signal averaging. In preliminary testing with paralysis in place (to record ENG only) 23 Hz was compared to 3.5 Hz, with no discernible difference between the evoked recordings.

Experiments were also conducted to investigate L6 vs S1 mapping/recruiting. In five experiments stimulation of the S1 and L6 nerves was delivered while recording from the EUS, sciatic nerve, sensory pudendal nerve, and motor pudendal nerve. Stimulation was conducted prior to paralysis to determine motor threshold. Stimulation for these experiments consisted of 23 Hz stimulation with biphasic pulses, 100 μs per phase. Stimulation polarity was alternated between pulses. Toggling stimulation polarity toggled the polarity of the stimulation artifact. Originally, a stimulus triggered average for all pulses was intended to be analyzed, with the artifact having been removed by averaging. However, responses nearly always were phase shifted which upon averaging led to distorted signals and some signal cancelation. Instead, the polarity toggling allowed for visual assessment of what was an artifact versus a response, rather than being used in quantitative analysis. For quantitative analysis the polarity with the larger response was analyzed.

Once motor threshold (1 T) had been established and appeared to be stable the animal was paralyzed as described above. Stimulation was then conducted at various amplitudes ranging from just below 1 T to a maximum of 3 T-10 T. Initially amplitude was varied in order from lowest to highest tested. In later experiments amplitudes were randomized. Stimulation was completed at one location (L6 or S1) before testing at the other location, with the order randomized between experiments.

The relative activation from L6 versus S1 stimulation was assessed by computing the average activity 1-10 ms after stimulation at 3 T. To compute the average activity, responses to all stimulation pulses were first averaged. Then the resulting signal was rectified and averaged from 1 ms to 10 ms after stimulus onset. A similar computation was done on the baseline period (10 ms to 1 ms before the stimulus onset) and the resulting baseline signal was subtracted from the computed activation value so that 0 corresponded to the activity at baseline. 3 T was chosen as it was the highest amplitude that was consistently tested. With the exception of one trace, the larger contributor to pudendal sensory or pudendal motor activation, either L6 or S1, remained constant across tested stimulation amplitudes.

Six cystometry experiments were conducted during the same time period when the mapping studies were conducted. After surgery the bladder was filled continuously with physiological saline at room temperature for at least 45 minutes. The pump rate was adjusted periodically so that voiding occurred once approximately every 4 minutes. The bladder was subsequently emptied and single-fill cystometrograms were conducted. The pump rate was set so that non-stimulation trials took 7-10 minutes from the start of filling until voiding occurred. The pump rate was maintained throughout blocks of stimulation and non-stimulation trials. Each trial consisted of a period of no bladder filling or stimulation (quiet period) lasting 1-3 minutes in duration, followed by filling, and the pump was stopped once a void or urine leaking occurred. When the bladder contraction ceased the bladder was manually emptied via aspiration through the filling line, and the residual volume was recorded. If the bladder remained contracted for an extended period of time (1 or 1.5 minutes, consistent within experiment), the trial was stopped, and the bladder was emptied. During studies in obese prone rats, voiding was allowed to occur for 90 seconds after initial urine loss. Voided volume was also collected and logged for each trial. Bladder capacity was calculated as the sum of the voided and residual volumes. Voiding efficiency was calculated as the voided volume divided by the bladder capacity.

Stimulation was conducted at 10 Hz throughout bladder filling and emptying. All stimuli delivered during cystometry used biphasic pulses with 100 us per phase. Unlike during mapping, stimulation polarity was not toggled. Stimulation amplitudes tested included 1 T, 1.5 T, and 2 T. Following stimulation, 1-3 non-stimulation trials were collected to allow assessment of any carry-over effects. Stimulation amplitudes were delivered in increasing order, with stimulation at L6 and S1 interleaved. The effects of sensory pudendal nerve stimulation were measured at the end of cystometric data collection to minimize any potential impact of this testing on the results of L6 and S1 stimulation.

After cystometric testing was complete mapping/recruitment testing was conducted. The approach was similar to the experiments in which only mapping/recruitment was conducted, except that only the sensory pudendal nerve and EUS were setup for recording.

Based on the results from the above experiments, an additional 4 CD rats underwent cystometric testing with stimulation of the L6-S1 trunk at higher amplitudes: 1-4 T and 6 T, at 10 Hz. Additionally, stimulation was conducted in a bursting pattern (3 pulses at 40 Hz, ~5 Hz between bursts), starting just prior to void onset. This stimulation pattern and timing has been used previously, on the motor pudendal branch, to increase voiding efficiency (Langdale and Grill, 2016; Gonzalez and Grill, 2017; Hokanson et al., 2021). In those experiments the minimum stimulation amplitude necessary to maximize evoked EUS EMG was used. This has typically been at or just slightly above 2 T. Thus, in these experiments stimulation amplitudes of 2 T and 3 T were tested. Similar to the previous cystometric testing, stimulation amplitudes were delivered from lowest to highest, with 2 T and 3 T bursting stimulation tested just before or after continuous stimulation at 2 T and 3 T at 10 Hz. No recruitment testing was conducted after these experiments.

This same process was repeated for 6 OP rats and 8 OR rats. For animals in which there was no clear contraction onset, bursting stimulation started after the first drop of urine was expelled. Bursting always continued until the end of the trial.

Pudendal motor bursting was tested in five additional OP rat experiments, as well as at the end (n=1) and beginning (n=1) of two previous OP experiments. Cystometric methods were the same as described above. The bursting pattern was the same as that used on the L6-S1 trunk, but the stimulation amplitude was chosen by finding the minimum amplitude that maximized the evoked EUS EMG activity.

In the last three experiments, trials with pudendal motor bursting were interleaved with L6-S1 bursting at 2 and 3 T. After data was collected prior to transection, the L6-S1 trunk was transected, central to the cuff so that afferent transmission from the L6-S1 trunk cuff was no longer possible, and the three stimulation patterns were again tested.

Bladder capacity and voiding efficiency values were averaged by trial type within an experiment. The resulting values were normalized to non-stimulation control trials. For statistical analysis these values were log-transformed. One-way ANOVAs were subsequently computed. Post-hoc testing compared all stimulation test types to the control condition, with Dunnett's test used to correct for multiple comparisons. Comparison of OP and OR voiding efficiency data was done using an unpaired t-test (two-tailed). For L6-S1 trunk stimulation, changes in bladder capacity and voiding efficiency as a function of stimulation amplitude were estimated using linear regression. Data are reported as means with 95% confidence intervals. For log-transformed data, the resulting means and 95% confidence intervals were exponentiated (inverse transformed) for easier interpretation. Most data analysis was done using MATLAB (2019a), including Boxplot figures, which were used for data visualization only and were not used for statistical calculations or to exclude data.

All statistical analyses were done using GraphPad (8.4.3). Statistical significance is reported as P<0.05.

Example 3

Figures 3A, 3B:
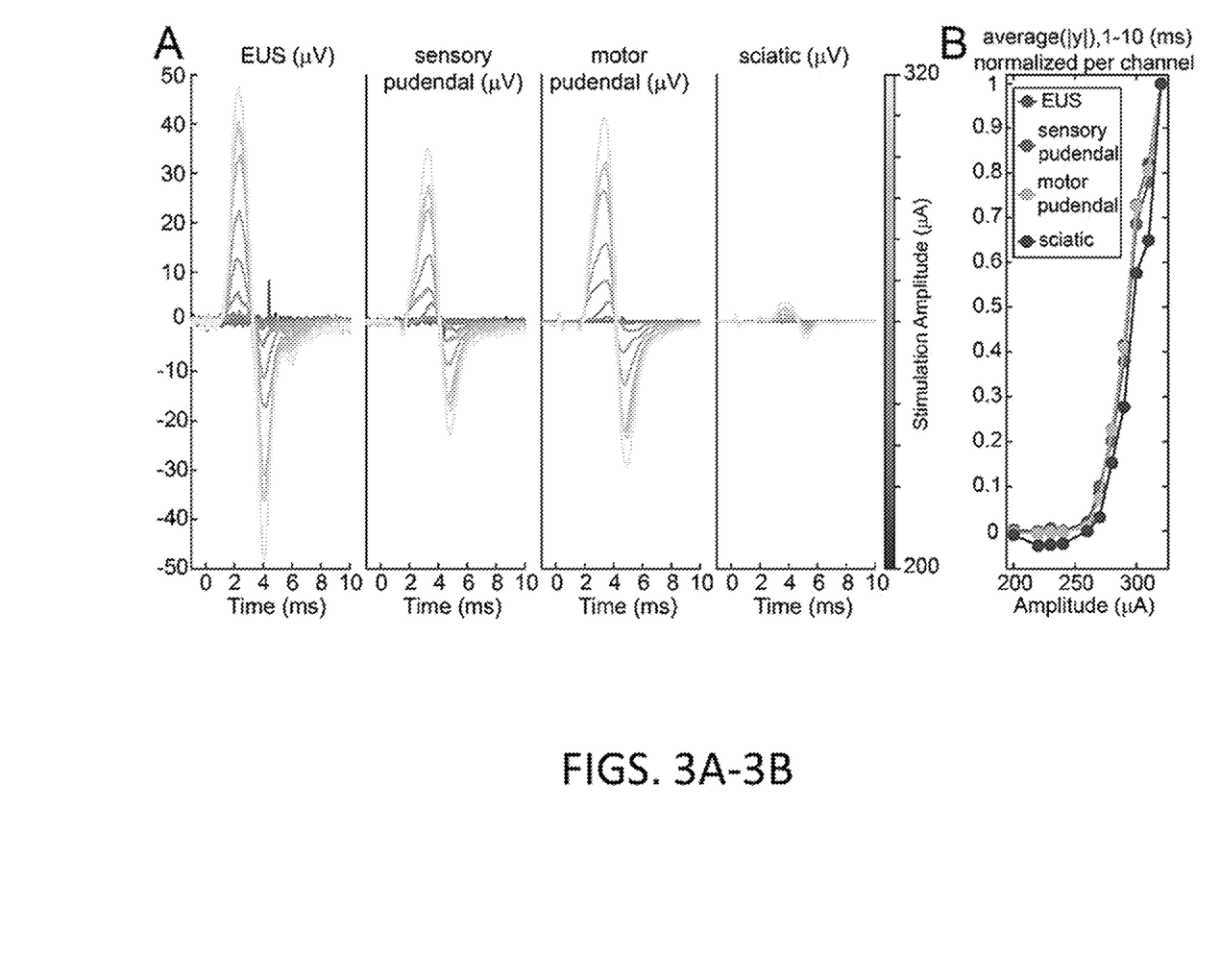
FIGS. 3A-3B: Recruitment from S1 stimulation via the foramen. Stimulus-triggered averages at four recording locations (A). Stimulation included a biphasic pulse, 40 µs per phase, repeated ~500× at 23 Hz. In this example, the movement threshold was at 270 µA. Input-output curves from all channels begin to increase at nearly the same amplitude, suggesting all recording channels are picking up broad EMG activity, via volume conduction, rather than local activity (B). Input-output curves were normalized to the maximum value on each channel, and 0 is average activity level observed just prior to each stimulus pulse. The activity level was quantified by averaging stimulation pulses, rectifying the resulting signal, then averaging over a time span of 1-10 ms following the stimulus onset.

In initial experiments, stainless steel wires were placed through the S1 foramen to stimulate the S1 nerve. In these experiments the goal was to evaluate recruitment of the pelvic and pudendal nerves as a function of stimulation amplitude, relative to activation of the sciatic nerve. As these experiments developed, cuffs were able to be placed on both the sensory and motor branches of the pudendal nerve, rather than a cuff around both branches together (i.e. compound pudendal nerve at the level of the fossa). From these initial set of experiments, several observations were made. First, stimulation of the S1 nerve caused strong tail motion. Although in one experiment distal tail curling was noticeable, in the majority of experiments the entire tail moved, suggesting more proximal control. This would be in line with the notion that a major function of the pelvic floor muscles in the rat is to control the tail (Thor and de Groat, 2010). Second, there was no obvious leg movements or toe curling, suggestive of minimal or no sciatic nerve activation. Thus, for this type of stimulation in rats, unlike people, the off-target motor effects appear to be primarily the tail rather than the leg and foot. Third, all recording channels appeared to activate simultaneously (FIG. 3). This suggested that without paralysis, as these experiments were conducted, recording channels picked up remote EMG activity (from volume conduction). Thus, even though nerve cuffs were used to record neural activity (ENG), most likely the majority of the recordings were muscle activity (EMG).

Figures 4A, 4B:
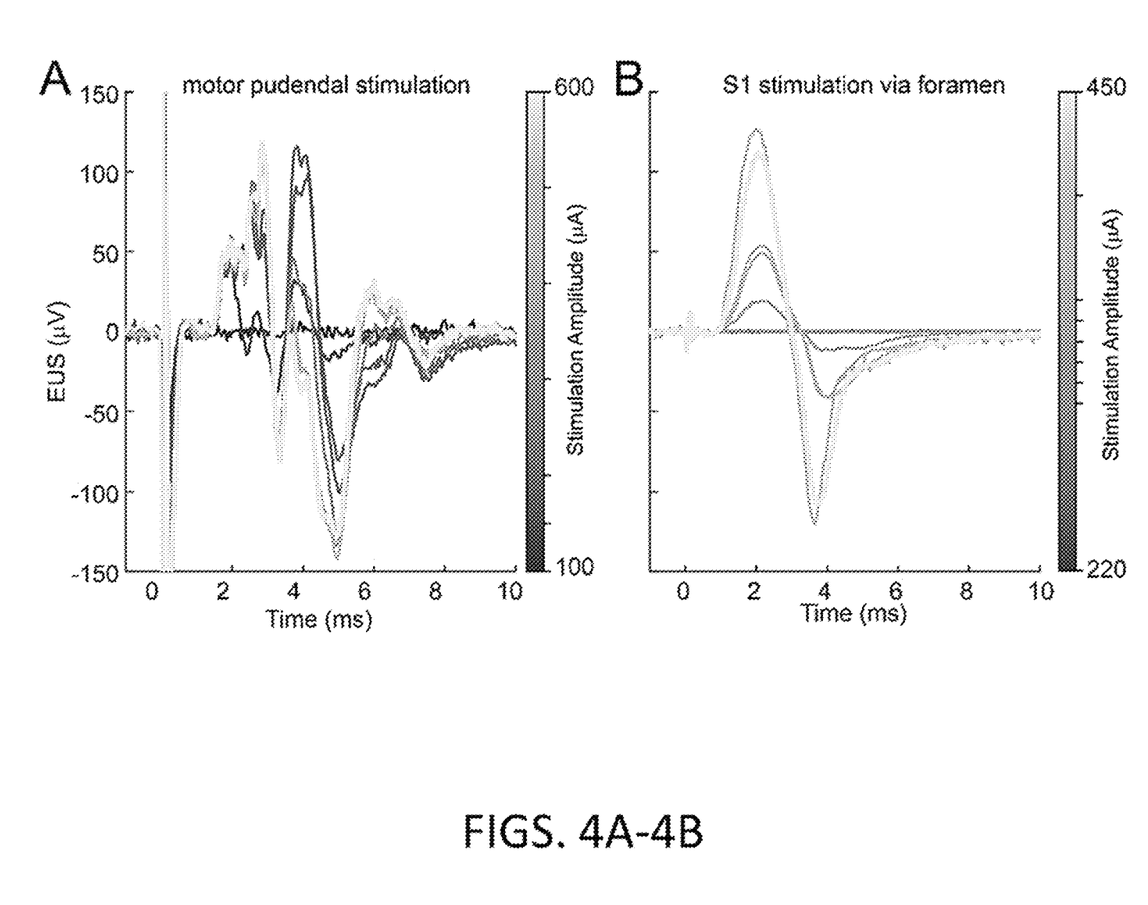
FIGS. 4A-4B: Stimulus triggered averaged signals from motor pudendal stimulation (A) and S1 stimulation (B), via foramen, recorded at the EUS. Stimuli were delivered at 23 Hz with biphasic pulses, 40 µs per phase. Data are from the same experiment and were collected sequentially within 1 h. The motor pudendal averages are polyphasic, spanning a time period of roughly 2-9 ms. S1 stimulation shows a simpler, biphasic activation, with considerably less activation after 4 ms.

Additionally, the activation patterns from S1 stimulation, as recorded on the EUS electrode, were noticeably different from activation patterns seen during direct motor pudendal stimulation. An example of this difference is shown in FIG. 4.

One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the present disclosure. Changes therein and other uses will occur to those skilled in the art which are encompassed within the spirit of the present disclosure as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

What is claimed is:

1. A method for determining electrode location for neural stimulation in a subject, the method comprising:
   electrically stimulating at least one peripheral nerve and recording electrical activity in at least one target nerve;
   electrically stimulating at least one target nerve and recording electrical activity in at least one peripheral nerve; and/or
   electrically stimulating at least one target nerve and recording at least one subject perception; and
   determining the at least one target nerve having the strongest representation associated with the at least one peripheral nerve and/or the strongest subject perception associated with the at least one peripheral nerve, wherein determining the at least one target nerve having the strongest representation associated with the at least one peripheral nerve comprises determining a sacral nerve side and level in the subject.

2. The method of claim 1, wherein the target nerve having the strongest representation associated with the at least one peripheral nerve and/or the strongest subject perception associated with the at least one peripheral nerve is the location determined to be where the electrode provides maximum therapeutic benefit.

3. The method of claim 2, wherein the therapeutic benefit comprises treating and/or preventing at least one symptom associated with overactive bladder, urge urinary incontinence, urinary urgency frequency, underactive bladder, urinary retention, fecal incontinence, constipation, and/or sexual dysfunction.

4. The method of claim 1, wherein the strongest representation associated with the at least one peripheral nerve corresponds to the largest recorded signal.

5. The method of claim 1, wherein the strongest subject perception associated with the at least one peripheral nerve comprises one or more of location, intensity, and/or character of the perception.

6. The method of claim 1, wherein the electrical stimulation comprises placement of an electrode lead adjacent to the target nerve or the peripheral nerve, followed by activation of a pulse generator.

7. The method of claim 1, wherein the recording of electrical activity comprises placement of at least one electrode lead adjacent to the target nerve or placement of at least one electrode lead adjacent to the peripheral nerve, followed by detection and quantification of the electrical activity in the target nerve or the peripheral nerve.

8. The method of claim 1, wherein the at least one target nerve comprises a sacral nerve.

9. The method of claim 1, wherein the at least one peripheral nerve comprises a pudendal sensory nerve.

10. The method of claim 9, wherein the pudendal sensory nerve is a dorsal genital nerve.

11. The method of claim 1, wherein the at least one peripheral nerve comprises a pudendal motor nerve.

12. The method of claim 1, wherein the at least one peripheral nerve comprises a tibial nerve or a saphenous nerve.

13. The method of claim 1, wherein the at least one subject perception corresponds to a specific location on the subject's body.

14. The method of claim 13, wherein the specific location on the subject's body comprises an area of the subject's genitals and/or pelvic muscles.

15. The method of claim 1, wherein the method further comprises placing an electrode lead adjacent to the target nerve having the strongest representation associated with the at least one peripheral nerve.

16. The method of claim 15, wherein the method further comprises delivering electrical stimulation to the target nerve to treat and/or prevent at least one symptom associated with overactive bladder, urge urinary incontinence, urinary urgency frequency, underactive bladder, urinary retention, fecal incontinence, constipation and/or sexual dysfunction.

17. A method of treating and/or preventing at least one symptom associated with a disease or condition, the method comprising:
    determining an electrode location for neural stimulation in a subject by electrically stimulating at least one peripheral nerve and recording electrical activity in at least one target nerve; electrically stimulating at least one target nerve and recording electrical activity in at least one peripheral nerve; and/or electrically stimulating at least one target nerve and recording at least one subject perception;
    determining the at least one target nerve having the strongest representation associated with the at least one peripheral nerve and/or the strongest subject perception associated with the at least one peripheral nerve, wherein determining the at least one target nerve having the strongest representation associated with the at least one peripheral nerve comprises determining a sacral nerve side and level in the subject; and
    placing an electrode in an area suitable to deliver electrical stimulation to the target nerve to treat and/or prevent at least one symptom in the subject.

18. The method of claim 17, wherein the target nerve having the strongest representation associated with the at least one peripheral nerve and/or the strongest subject perception associated with the at least one peripheral nerve is the location determined to be where the electrode provides maximum therapeutic benefit.

19. The method of claim 17, wherein the strongest representation associated with the at least one peripheral nerve corresponds to the largest recorded signal.

20. The method of claim 17, wherein the strongest subject perception associated with the at least one peripheral nerve comprises one or more of location, intensity, and/or character of the perception.

21. The method of claim 17, wherein the recording of electrical activity comprises placement of at least one electrode lead adjacent to the target nerve or placement of at least one electrode lead adjacent to the peripheral nerve, followed by detection and quantification of the electrical activity in the target nerve or the peripheral nerve.

22. The method of claim 17, wherein the at least one target nerve comprises a sacral nerve.

23. The method of claim 17, wherein the at least one peripheral nerve comprises a pudendal sensory nerve.

24. The method of claim 17, wherein the at least one subject perception corresponds to a specific location on the subject's body.

25. The method of claim 24, wherein the specific location on the subject's body comprises an area of the subject's genitals and/or pelvic muscles.

26. The method of claim 17, wherein the disease or condition comprises overactive bladder, urge urinary incontinence, urinary urgency frequency, underactive bladder, urinary retention, fecal incontinence, constipation and/or sexual dysfunction.

* * * * *